(12) United States Patent
King (10) Patent No.: US 9,162,995 B2
(45) Date of Patent: Oct. 20, 2015

(54) FORMATION OF HIGHER MOLECULAR WEIGHT CYCLIC POLYAMINE COMPOUNDS FROM CYCLIC POLYAMINE COMPOUNDS

(71) Applicant: Dow Global Technologies LLC, Midland, MI (US)

(72) Inventor: Stephen W. King, League City, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 14/369,622

(22) PCT Filed: Nov. 14, 2012

(86) PCT No.: PCT/US2012/064971
§ 371 (c)(1),
(2) Date: Jun. 27, 2014

(87) PCT Pub. No.: WO2013/101345
PCT Pub. Date: Jul. 4, 2013

(65) Prior Publication Data
US 2015/0011762 A1    Jan. 8, 2015

Related U.S. Application Data

(60) Provisional application No. 61/581,323, filed on Dec. 29, 2011.

(51) Int. Cl.
*C07D 241/04* (2006.01)
*C07D 295/13* (2006.01)

(52) U.S. Cl.
CPC .................................. *C07D 295/13* (2013.01)

(58) Field of Classification Search
CPC ..................................................... C07D 241/04
USPC ................................................. 544/358, 402
See application file for complete search history.

(56) References Cited

U.S. PATENT DOCUMENTS

| 4,568,746 A | 2/1986 | Cowherd, III |
| 4,863,890 A * | 9/1989 | Koll ............................. 502/230 |
| 4,973,692 A | 11/1990 | Burgess et al. |
| 4,977,266 A | 12/1990 | Burgess et al. |
| 4,992,587 A * | 2/1991 | Koll ............................. 564/398 |
| 5,196,588 A | 3/1993 | Burgess et al. |
| 5,256,786 A | 10/1993 | Bowman et al. |
| 5,410,086 A | 4/1995 | Burgess |
| 6,465,601 B1 | 10/2002 | Wiesendanger et al. |
| 6,534,441 B1 | 3/2003 | Bartley et al. |
| 7,053,247 B2 | 5/2006 | Lif et al. |
| 8,187,997 B2 | 5/2012 | King et al. |
| 8,188,318 B2 | 5/2012 | Petraitis et al. |
| 8,293,676 B2 | 10/2012 | King et al. |
| 8,383,861 B2 | 2/2013 | Do et al. |
| 2008/0004362 A1 | 1/2008 | Masuda et al. |
| 2008/0132725 A1 | 6/2008 | Melder et al. |
| 2010/0087683 A1 | 4/2010 | Cook et al. |
| 2010/0094007 A1 | 4/2010 | King et al. |
| 2014/0357750 A1 | 12/2014 | King et al. |
| 2015/0005404 A1 | 1/2015 | Latham et al. |

FOREIGN PATENT DOCUMENTS

| EP | 0 412 611 | 2/1991 |
| EP | 0 414 574 | 2/1991 |
| EP | 0 737 669 | 10/1996 |
| GB | 1508460 | 4/1978 |
| GB | 1551127 | 8/1979 |
| WO | WO 2010/042157 | 4/2010 |
| WO | WO 2013/102053 | 7/2013 |
| WO | WO 2013/102097 | 7/2013 |

OTHER PUBLICATIONS

Bazzicalupi, C., et al., (1998) *Reinforced piperazine rings containing polyamines: metal complex equilibria and structural studies*, Inorganica Chimica Acta 268: 63-68.
Marchand, A.P., et al., (2004) *Synthesis and Electrospray Ionization Mass Spectrometric Evaluation of the Metal Cation Complexation Behavior of Cage-Annulated Azacrown Ethers*, Heterocycles 62: 279-296.

* cited by examiner

*Primary Examiner* — Golam M M Shameem
(74) *Attorney, Agent, or Firm* — Kagan Binder, PLLC (57) ABSTRACT

The present invention provides strategies for making higher weight, cyclic polyamines from lower molecular weight, cyclic polyamine starting compounds via transamination. The higher molecular weight, cyclic polyamines are structurally similar to the lower molecular weight, cyclic polyamine starting compounds. The reactants used in the present invention include a cyclic polyamine component that comprises at least two amine groups separated from one another by at least a binary carbon atom spacing, and that can be transaminated to form a higher molecular weight, cyclic polyamine compound. The higher molecular weight, cyclic polyamine has at least two cyclic rings joined to one another through a nitrogen-containing hydrocarbyl group. Each of the cyclic rings contains two amine groups separated from one another by binary carbon atom spacing.

13 Claims, 2 Drawing Sheets

FORMATION OF HIGHER MOLECULAR WEIGHT CYCLIC POLYAMINE COMPOUNDS FROM CYCLIC POLYAMINE COMPOUNDS

This application claims benefit from International Application No. PCT/US2012/064971, which was filed on Nov. 14, 2012, which in turn claims priority to U.S. Provisional Patent Application Ser. No. 61/581,323, filed Dec. 29, 2011, the disclosures of which are incorporated herein by reference.

FIELD OF THE INVENTION

The present invention relates to higher molecular weight, cyclic polyamine compounds, processes that use transamination to prepare higher molecular weight, cyclic polyamine compounds from lower molecular weight, cyclic polyamine starting compounds, and to compositions useful in the manufacture of such higher molecular weight, cyclic polyamine compounds.

BACKGROUND OF THE INVENTION

A variety of techniques are known and can be used to prepare a variety of amine compounds and mixtures of amine compounds from lower molecular weight amines. For example both transamination and reductive amination techniques can be used to provide acyclic and/or cyclic amine products.

For example, GB Patent No. 1508460 discloses the transamination of ethylenediamine (EDA). U.S. Pat. Nos. 4,568,746 and 7,053,247 also discloses the transamination of EDA. GB Patent No. 1551127 discloses the transamination of 1,3-diaminopropane (1,3-DAP). U.S. Pat. No. 6,465,601 discloses the preparation of mixed amines by the transamination of a substituted phenolic compound (Mannich base) with another amine. The mixed amines are useful as accelerators for curable epoxy and polyurethane systems. US 2008/0132725 A1 discloses the preparation of bis(3-aminopropyl) amine (dipropylenetriamine, DPTA) by the continuous reaction of 1,3-propylenediamine in the presence of a heterogeneous catalyst in a reaction column. None of these publications disclose the preparation of higher molecular weight, cyclic polyamines from lower molecular weight, cyclic polyamine compounds of the present invention. In fact, they generally teach processes wherein such materials are not made or if made can be redecomposed to the dimers and trimers under the reaction conditions employed.

Reductive amination is typically used to prepare ethyleneamines from a feed stream of one or more alkanolamines. The resultant product of this process typically comprises a mixture of both acyclic and cyclic amines.

While these techniques have proven to be viable ways to manufacture amines on an industrial scale, several challenges remain. For example, the starting materials in transamination typically produce complex mixtures of both cyclic polyamines and acyclic polyamines generally and discourage the formation of higher molecular weight, acyclic polyamines due to disproportionation and cyclic formation. The reaction mixture then must be separated into individual components (usually via distillation) since cyclic species are desired for some applications, and acyclic species are desired for other applications. For example, acyclic amines such as diethylenetriamine and triethylenetetramine formed from the transamination of ethylenediamine or the reductive amination of monoethanolamine are useful intermediates for wet strength resins and corrosion inhibitors. Cyclic polyamines are useful as epoxy hardeners. Additionally, they are a critical component in gas treating formulations for $CO_2$ capture. In addition, because of their reactivity, cyclic polyamines are often used as intermediates for a variety of derivatives used in other applications. For example, methylation of piperazine (PIP) provides N,N'-dimethylpiperazine which is a useful polyurethane catalyst. Alkoxylation of PIP provides a starting material for polyurethanes, and reactions with diacids provide polyamides for use as hot-melt adhesives.

PIP is a solid at ambient (i.e., room) temperature, and can be a challenge to offer as a solid (e.g., flaking, prilling etc.). As a result, PIP is currently commercially offered by the DOW Chemical Company as a 68% aqueous solution (PIP68). However, the aqueous nature of the product limits its use in several applications that require anhydrous PIP due to time and energy costs to remove the water. Anhydrous PIP is a solid at room temperature and can be difficult to handle in many applications because of limited solubility in most common solvents.

As a result, there is a need to provide methodologies to provide compositions that have similar reactivity and functionality as PIP while being liquids at ambient temperature.

SUMMARY OF THE INVENTION

The present invention provides improved strategies for preparing higher molecular weight, cyclic polyamine products. Such higher molecular weight, cyclic polyamine products may comprise mixtures of the higher molecular weight, cyclic polyamines and lower molecular weight, cyclic polyamines.

The strategies of the present invention provide higher molecular weight, cyclic polyamines that are structurally similar to that of the starting cyclic polyamine, have similar reactivity to that of the starting cyclic polyamine, and have the benefit of being a liquid at room temperature. Additionally, the higher molecular weight, cyclic polyamine comprises at least two cyclic polyamine rings. It is expected that any extra amine functionality in the molecule will impart additional properties that are not present in the starting cyclic polyamine. Additionally, in some embodiments, the higher molecular weight, cyclic polyamine will have fewer volatile organic compound (VOC) issues than the lower molecular weight, cyclic polyamines or other lower molecular weight amines.

The present invention is based in part upon using reactants that include a cyclic polyamine component that comprises at least two amine groups separated from one another by at least a binary carbon atom spacing, and that can be transaminated to form a higher molecular weight, cyclic polyamine compound. The higher molecular weight, cyclic polyamine has at least two cyclic rings joined to one another through a nitrogen-containing hydrocarbyl group. Each of the cyclic rings contains two amine groups separated from one another by binary carbon atom spacing.

The reaction mixture further comprises at least one hydrogenation/dehydrogenation catalyst. Useful hydrogenation/dehydrogenation catalysts include both transamination and reductive amination catalysts.

As used herein, the term polyamine refers to a compound that includes at least two amine groups.

As used herein, the term "carbon atom spacing" refers to the number of carbon atoms between the various functional groups. For example, the term binary spacing refers to a two carbon atom spacing; the term ternary spacing refers to a three carbon atom spacing; etc. The binary, ternary, or other carbon atom spacing is that portion of the particular molecule that separates the various functional groups therein.

As used herein, the term high molecular weight refers to the molecular weight of a polyamine product(s) resulting from the practice of the present invention.

In one aspect, the present invention provides a reaction product comprising a higher molecular weight cyclic polyfunctional amine having the generic Formula I and optionally an amine having the generic Formula II wherein each R, T, U, V, W, X, Y, and Z group is the same or different and is selected from hydrogen, or a hydrocarbyl group; and the value of x is 0 to 10, with the proviso that if x is greater than 1, each T may be the same or different, the polyfunctional amine comprising the reaction product of:

(a) an amine of the generic Formula III wherein each R, T, U, V, W, X, Y, and Z group is as described above; and the value of x is as described above; and (b) a hydrogenation/dehydrogenation catalyst.

In another aspect, the present invention provides a reaction composition comprising

(a) an amine of the Formula III wherein each R, T, U, V, W, X, Y, and Z group is the same or different and is selected from hydrogen, or a hydrocarbyl group; and the value of x is 0 to 10, with the proviso that if x is greater than 1, each T may be the same or different; and (b) a hydrogenation/dehydrogenation catalyst.

In still another aspect, the present invention comprises a method of manufacturing a polyfunctional amine having the Formula I and, optionally, an amine having the Formula II wherein each R, T, U, V, W, X, Y, and Z group is the same or different and is selected from hydrogen, or a hydrocarbyl group; and the value of x is 0 to 10, with the proviso that if x is greater than 1, T may be the same or different, the method comprising the steps of:

(a) providing an amine of the Formula III wherein each R, T, U, V, W, X, Y, and Z group is as described above; and the value of x is as described above; and (b) causing transamination of the amine of Formula III in the presence of a hydrogenation/dehydrogenation catalyst under conditions effective to cause the formation of the amine of Formula I.

DETAILED DESCRIPTION OF THE PRESENTLY PREFERRED EMBODIMENTS

Figure 1:
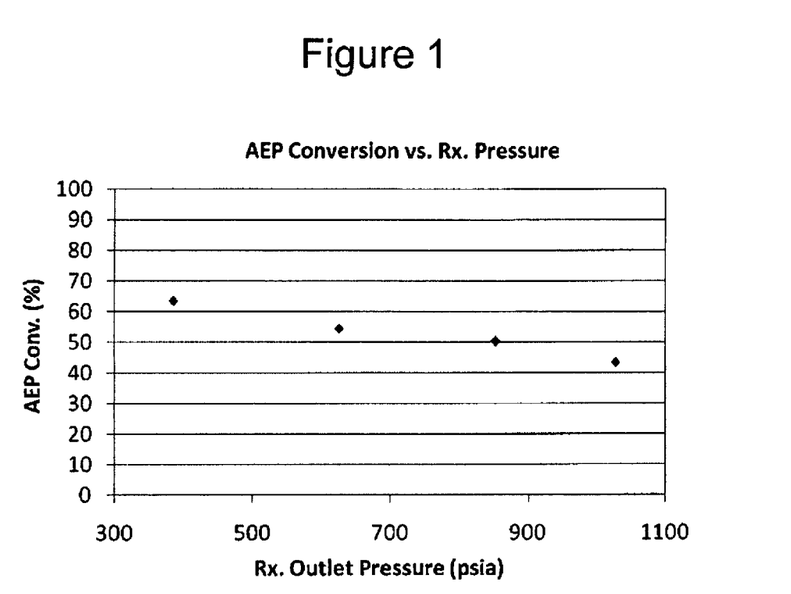
FIG. 1 is a graph showing AEP conversion (%) at increasing outlet reaction pressures (psia) and reflecting that under similar reaction conditions higher conversions of AEP are obtained at lower pressures.
Figure 2:
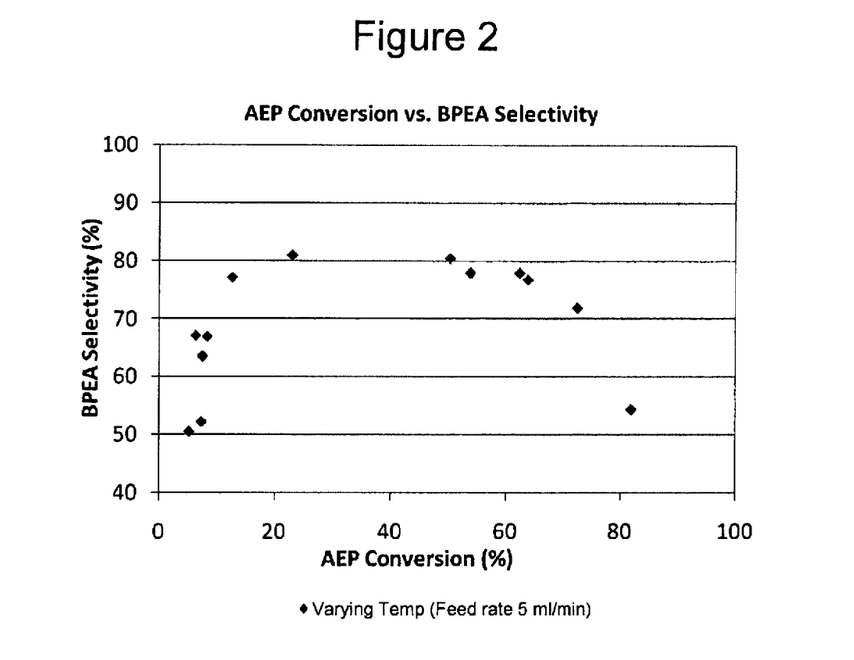
FIG. 2 is a graph showing BPEA selectivity (%) at increasing AEP conversion (%) and reflecting that at a constant pressure and feed rate, BPEA selectivity reaches a maximum at ca. 20% AEP conversion and remains essentially flat to 65% AEP conversion.

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods, materials, and compositions described.

Unless defined otherwise herein, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

The present invention provides strategies for making cyclic polyamine compounds that have a higher molecular weight than the molecular weight of a starting cyclic polyamine by methodologies that comprise transaminating a first or lower molecular weight, cyclic polyamine compound that has at least two amine groups separated from one another by a binary carbon spacing (C2 spacing) in the cyclic ring to produce a second or higher molecular weight, cyclic polyamine compound. The second polyamine compound comprises at least two cyclic rings that each have at least two amine groups separated from one another by a binary carbon spacing (C2 spacing) in each cyclic ring.

Formula III, set forth above, represents an example of first cyclic polyamine compounds useful in the invention. Formula I and II, set forth above, represents an example of the second cyclic polyamine compounds produced by the present invention.

Hydrocarbyl groups that may be used in the practice of the invention may be substituted or unsubstituted, linear, branched, or cyclic hydrocarbyl such as alkyl, aryl, aralkyl, or the like; a monovalent moiety including one or more heteroatoms; polyether chains comprising one or more oxyalkylene repeating units such as —$R^1O$—, wherein R is often alkylene of 2 to 5 carbon atoms; other oligomeric or polymer chains of at least 2 repeating units. Preferably, R, $R^1$, T, U, V, W, X, and Y are H or straight, branched, or cyclic hydrocarbyl such as alkyl of 1 to 10 carbon atoms, preferably 1 to 3 carbon atoms. More preferably, R, $R^1$, T, U, V, W, X, and Y are H.

The values of x in the practice of the invention are typically in the range of from 1 to 10, preferably in the range of from 2 to 5, and more preferably in the range of from 2 to 3.

Examples of first or lower molecular weight, cyclic polyamines useful in the present invention include 2-(piperazin-1-yl)ethanamine (AEP), 3-(piperazin-1-yl)propan-1-amine, 4-(piperazin-1-yl)butan-1-amine, 5-(piperazin-1-yl)pentan-1-amine, 6-(piperazin-1-yl)hexan-1-amine, 1-(piperazin-1-yl)propan-2-amine and 2-(piperazin-1-yl)propan-1-amine.

Examples of second or higher molecular weight, cyclic polyamines consistent with Formula I that are produced by the present invention include bis(2-(piperazin-1-yl)ethyl)amine (BPEA) (3-(piperazin-1-yl)propyl)amine, bis(4-(piperazin-1-yl)butyl)amine, bis(5-(piperazin-1-yl)pentyl)amine, bis(6-(piperazin-1-yl)hexyl)amine, bis(1-(piperazin-1-yl)propan-2-yl)amine, and bis(2-(piperazin-1-yl)propyl)amine.

Examples of second or higher molecular weight, cyclic polyamines consistent with Formula II that are produced by the present invention include 2-(4-(2-(piperazin-1-yl)ethyl)piperazin-1-yl)ethanamine, 3-(4-(3-(piperazin-1-yl)propyl)piperazin-1-yl)propan-1-amine, 4-(4-(4-(piperazin-1-yl)butyl)piperazin-1-yl)butan-1-amine, 5-(4-(5-(piperazin-1-yl)pentyl)piperazin-1-yl)pentan-1-amine, 6-(4-(6-(piperazin-1-yl)hexyl)piperazin-1-yl)hexan-1-amine, 1-(4-(1-(piperazin-1-yl)propan-2-yl)piperazin-1-yl)propan-2-amine, and 2-(4-(2-(piperazin-1-yl)propyl)piperazin-1-yl)propan-1-amine.

Any hydrogenation/dehydrogenation catalyst that can catalyze a transamination reaction can be used in the present invention. Such catalysts are well known. Hydrogenation generally refers to a chemical reaction involving the addition of hydrogen, and the process is often used to reduce or saturate organic materials. The reverse reaction in which hydrogen is removed from an organic molecule is referred to as dehydrogenation.

Useful hydrogenation/dehydrogenation catalysts include transamination catalysts and reductive amination catalysts. Platinum group metals, particularly platinum, palladium, rhodium, and ruthenium form highly active hydrogenation/dehydrogenation catalysts. These are known to operate at lower temperatures and lower pressures of $H_2$. Non-precious metal catalysts, especially those based on nickel (such as Raney nickel and Urushibara nickel) have also been developed as economical alternatives. Other hydrogenation/dehydrogenation catalysts might incorporate iron, copper, chromium, molybdenum, cobalt, osmium, iridium, and/or the like.

In some aspects, the selectivity of the catalyst composition may be further enhanced by the use of metal promoter. The promoter may be a metal (or oxide) which when incorporated into the catalyst composition further enhances the productivity and/or selectivity in the amination reaction. As an example, metals or metal oxides for use as promoters, in addition to the hydrogenation/dehydrogenation catalyst, are compounds containing elements selected from Group IA, Group IIA, Group IIIA, Group IVA, Group VA, Group VIA, Group IB, Group IIB Group IIIB, Group IVB, Group VB, Group VIB, Group VIIB and Group VIIIB of the Periodic Table (IUPAC format). Exemplary metals include, for example, copper, cobalt, chromium, rhodium, iridium, ruthenium, zinc, palladium, platinum, sodium, calcium, magnesium, strontium, lithium, potassium, barium, cesium, lanthanum, tungsten, iron, silver, titanium, manganese, niobium, aluminum, tin and mixtures of these metals. Some particularly useful metals include magnesium, zinc, niobium, iridium, ruthenium, platinum palladium, rhenium, cobalt, copper, tin and mixtures thereof.

Promoters can be added to the catalyst composition either by co-impregnation with the hydrogenation/dehydrogenation metal or they can be added to the support either before or after incorporation of the hydrogenation/dehydrogenation metal salts. The hydrogenation/dehydrogenation metal and the promoter need not be added simultaneously with each other; the hydrogenation/dehydrogenation metal and promoter combination can be added in any sequence. Promoters can be added to the catalyst composition at desirable levels, which are generally no higher than the hydrogenation/dehydrogenation metal present in the catalyst composition on a weight percent basis.

Catalysts can be heterogeneous, homogeneous, or a combination of these may be used. Homogeneous catalysts dissolve in the reaction medium. Illustrative homogeneous catalysts include the rhodium-based compound known as Wilkinson's catalyst and the iridium-based Crabtree's catalyst. Heterogeneous catalysts are solids that are caused to contact the reaction medium, which may be in liquid, gas or other fluid form.

Heterogeneous catalysts are preferred. Often, heterogeneous catalysts comprise one or more catalytic materials supported upon a suitable substrate. The substrate may be used in various shapes or combinations such as, for example, powder, particle, pellet, granule, extrudate, fiber, shell, honeycomb, plate, or the like. The particles can be regular in shape, irregular, dendritic, dendrite-free, or the like. Preferred supports are particulate in nature or powders.

In particularly preferred embodiments, the catalyst material is heterogenous and incorporates a hydrogenation/dehydrogenation metal that is nickel and a promoter that is rhenium on a support material. The weight ratio of nickel to rhenium may vary over a wide range. For instance, the weight ratio of nickel to rhenium may be in the range from about 1:1000 to 1000:1, preferably 1:100 to 100:1, more preferably 1:50 to 50:1. Even more desirably, the weight ratio of nickel to rhenium is within these ranges with the proviso that the weight ratio is also greater than 1:1. In some preparations of the catalyst composition, the catalyst portion includes a mixture of nickel and rhenium in the composition in a predetermined weight ratio. In some cases, the weight ratio of the nickel and rhenium in the composition is in the range of about 3:1 to about 15:1. In some aspects, nickel is present in an amount in the range of about 23 weight percent to about 2 weight percent, and rhenium is present in the composition in the range of about 7 weight percent to about 0.5 weight percent. In some aspects, nickel is present in an amount in the range of about 5 weight percent to about 8.5 weight percent, and rhenium is present in the composition in the range of about 2.5 weight percent to about 1 weight percent. An exemplary catalyst portion includes nickel at about 6.8 weight percent and rhenium at about 1.8 weight percent.

In preferred embodiments in which a heterogeneous catalyst incorporates nickel and rhenium, useful support materials include silicas, aluminas, titanias, zirconias, magnesias, carbons, molecular sieves, or mixtures thereof.

In preferred embodiments in which a heterogeneous catalyst incorporates nickel and rhenium, a useful support are alumina-silicate particles. Such catalysts and methods of making such heterogeneous catalysts on such supports are further described in U.S. Pat. No. 6,534,441. Such catalysts are also further described in United States Published Patent Application Nos. 2010-0137642-A1, titled "LOW METAL LOADED, ALUMINA SUPPORTED, CATALYST COMPOSITIONS AND AMINATION PROCESS" by Stephen W. King et al.; 2010-0087682-A1, titled "LOW METAL CATALYST COMPOSITIONS INCLUDING ACIDIC MIXED METAL OXIDE AS SUPPORT" by Steven W. King et al.; 2010-0087683-A1, titled "A PROCESS TO SELECTIVELY MANUFACTURE DIETHYLENETRIAMINE (DETA) OR OTHER DESIRABLE ETHYLENAMINES VIA CONTINUOUS TRANSAMINATION OF ETHYLENEDIAMINE (EDA), AND OTHER ETHYLENEAMINES OVER A HETEROGENEOUS CATALYST SYSTEM" by Ronald Gary Cook et al.; 2010-0087684-A1; (DOW0019P1) titled "METHODS FOR MAKING ETHANOLAMINE(S) AND ETHYLENEAMINE(S) FROM ETHYLENE OXIDE AND AMMONIA, AND RELATED METHODS" by David Do et al.; and 2010-0087681-A1, titled "Method Of Manufacturing Ethyleneamines" by David M. Petraitis et al.

In some modes of practice the metals of the catalytic portion are deposited on the support using an incipient wetness technique, often referred to as incipient wetness impregnation (IW or IWI). In this technique an active metal precursor (or combination of active metal precursors) is dissolved in an aqueous or organic solution. The metal-containing solution ("impregnation solution") is added to a catalyst support. Often, the impregnation solution is added in a volume that is the same as the pore volume of the support. Capillary action draws the impregnation solution into the pores of the support. The impregnated support can then be dried and calcined to drive off the volatile liquids of the impregnation solution. This process deposits the catalytic metals on the surface of the support portion.

In some modes of practice, the impregnation solution is an aqueous solution of a salt of the metal. Since more than one metal is to be immobilized on the support, the impregnation solution can include a mixture of salts of the desired metals. Alternatively, more than one impregnation solution can be prepared. The impregnation solution can be saturated with the metal salts, or the metal salts can be used in amounts less than saturation. The concentration of the metal salts in the impregnation solution can depend on factors such as the desired amount of metal(s) to be deposited on the support, and the solubility of the particular metal salt(s) used in the process.

Organic and inorganic salts of nickel include, but are not limited to, nickel nitrate hexahydrate, nickel formate, nickel acetate tetrahydrate, nickel acetate, nickel chloride, nickel carbonate and the like. A nickel-containing impregnation solution can be prepared containing one or more of these nickel salts. In some modes of practice, nickel nitrate or nickel formate is used to prepare the impregnation solution.

Precursor salts of rhenium include potassium and ammonium salts. Additionally, perrhenic acid may also be used. A rhenium-containing impregnation solution can be prepared containing one or both of these salts.

In many modes of practice, the one or more metals to be deposited on the support are dissolved in a suitable solvent, such as deionized water, for preparation of the impregnation solution.

One or more impregnation solutions can be prepared to provide the types and total amount of metals to be deposited on the support portion. Since a lower amount of metal is associated with the support, the total amount of metal can be deposited in a limited number of applications. For example, the total amount of metal deposited can be applied in one, two, three, or four applications. Although an impregnation solution can be prepared with a high concentration of metal salt (i.e., a minimal amount of water), in some cases the total amount of the impregnation solution to be applied may be more than what the alumina support can hold by absorption. Therefore, in some modes of practice, the impregnation solution is applied to the support in multiple steps, wherein a portion of the impregnation solution about equal to the absorption volume of the support is applied to the support in one application step. Incorporation of additional metal(s) into the support may be further increased by techniques known to those skilled in the art, such as increasing the time the support is in contact with the solution.

The impregnation solution can be applied to the support using various methods. For example, the solution can be applied by drip application, by immersion (e.g., dipping), or by spraying. During application, processes such as mixing, tumbling, stirring, or shaking can be used to agitate the support. Mechanical equipment can be used to facilitate agitation. Agitation during the application of the impregnation solution can increase the uniformity of the impregnation solution applied to the support.

After all or a portion of the impregnation solution is applied to the support, the support can be dried. In the drying step, the liquid which solvates the metal salt is volatized and removed from the support. The drying may be accomplished by any technique that sufficiently evaporates the volatile constituents of the impregnation solution. The drying step can comprise a calcination step, as further discussed herein. Multiple drying steps can be performed if the impregnation solution is applied in more than one step. Therefore, an overall process for preparing the catalyst composition can include multiple steps of disposing the application composition, and then drying the impregnated support. The steps of depositing and then drying can be performed until all of the impregnation solution is used.

Typically, the impregnated support is dried at a temperature of above 100° C. The elevated temperature can also be accompanied by a reduced pressure environment to accelerate removal of the liquid from the support. The support can be dried in air or in the presence of an inert gas, such as nitrogen. Drying is carried out for a period of time sufficient for removal of most or all of the liquid of the impregnation solution. In some modes of practice, the step of drying is performed for a period of about one hour or more at elevated temperatures.

The process of preparing the catalytic composition can also involve one or more steps of calcining the support. One or more steps of calcining the support can be performed in the absence of the catalytic metals, and optionally in the presence of the catalytic metals, or both.

In some modes of practice, given the high heat of calcination, drying and removal of the liquid component of the impregnation solution occurs. Therefore, as used herein, calcination of the support meets the requirements of the drying step or steps, which are typically performed following application of the impregnation solution. In addition, calcination can cause conversion of the metal salts into oxides. The choice of a particular calcination temperature can depend on the decomposition temperature of the salts used.

Calcination normally takes place at temperatures below the melting point of the materials used to form the support portion of the catalytic composition. For example, calcination is typically performed in the range of about 200° C. to about 1200° C., and more typically in the range of about 300° C. to about 500° C. A calcination step can take a period of time in the range of a minute to hours (e.g., two or three or more hours). Calcination can be carried out in the presence of air, or under inert gas.

In some modes of practice calcination is performed after one or more steps of applying the impregnation solution. After all of the impregnation solution has been applied the metal-loaded support can be calcined for a longer period of time to ensure substantial removal of the impregnation solution liquid. For example, in some specific modes of practice, the impregnation solution is applied to the support in two or more steps, with calcination at about 340° C. for about one hour in air performed after each step of applying, with a final calcination at about 340° C. for about one hour in air.

Following metal impregnation and calcination, the catalyst composition can be reduced, converting the metal oxides produced in the calcination step to the reduced metal form. Typically, the metal-containing support is reduced in the presence of hydrogen. The metal-containing support can be contacted with hydrogen gas at a temperature that is about in the same range as that used for calcination. The process of reduction can be carried out from about 30 minutes to about 24 hours, or more.

Following reduction, the catalyst composition can be stabilized with gentle oxidation. Typical stabilizing treatments involve contacting the reduced catalyst composition with oxygen or carbon dioxide. For example, in one mode of practice, the catalyst composition is treated with about 1% $O_2/N_2$. Prior to using in an amination reaction, the catalyst composition can be activated with hydrogen.

After impregnation and drying/calcination (with optional reduction) the catalyst composition can optionally be stored or handled in an inert environment.

In some embodiments, the morphology of the catalyst composition can be controlled to reduce or minimize mass transfer resistance during transamination. Some illustrative methods for addressing mass transfer resistance include: adjusting the morphology of the catalyst composition, selecting the form of the catalyst composition (e.g., by providing a thin coating of the active catalyst metals on the surface of the support), and/or the selecting the size of the catalyst particles. For example, PCT Publication No. WO 2006/060206 ("Transitional Alumina Particulate Materials Having Controlled Morphology and Processing for Forming Same," Bauer et al.) describes alumina particulate material that contains particles comprising transitional alumina having an aspect ratio of not less than 3:1 and an average particle size of not less than about 110 nm and not greater than 1000 nm. Various shaped particles are described, including needle-shaped particles and platy-shaped particles.

In other embodiments, the catalyst portion is deposited on a porous support portion so that at least the active catalyst metals are provided in a very thin outer layer or "egg shell" structure, so as to minimize mass transfer resistance for the amine-containing solution. This catalyst structure can also lower the active metal requirement for the catalyst composition, and/or maximize contact of the active metals with the amine-containing elements within the reaction solution.

Thus, in accordance with these embodiments, useful catalyst composition diameters can be in the range of about 0.8 mm to about 3.1 mm; surface area can be in the range of about 10 $m^2/g$ to about 200 $m^2/g$; catalytically active metal concentration can be in the range of about 1 weight percent to about 25 weight percent, and the catalyst portion can be provided as a thin outer shell on the support portion.

Methods described in U.S. Pat. No. 5,851,948 can be utilized to create a similar "egg shell" structure for the present inventive catalyst compositions. For example, the catalytic metals comprising the catalyst portion (here, nickel and rhenium) can be added to the support portion as a thin outer layer or shell on the support portion. This small thickness for the catalyst portion can be influenced by the flow characteristics of the nickel and rhenium salts and a suitable carrier liquid solution of an alcohol and water, the porosity and surface area of the support portion, and the diffusion rate of the active metal liquid solution into the porous support portion. The flow characteristics of the nickel and rhenium in the alcohol-water carrier liquid having low surface tension is controlled so as to initially form a "cluster"-type structure of the nickel and rhenium in the carrier liquid on only the outer surface of the support portion. Such "cluster" type structures are formed because of valence differences between ions of the active nickel and rhenium and molecules of the alcohol carrier liquid, and such larger "clusters" effectively impede penetration of the active metal into smaller size pores of the support material. During the subsequent drying, reducing and calcining steps for making the catalyst, the carrier liquid is destroyed and removed so that only the active metals remain in uniformly dispersed sites in the thin outer "egg-shell" structure on the support portion. Suitable alcohol carrier liquids may include ethanol, methanol and isopropanol.

This technique of depositing an active metal such as nickel and/or rhenium in a thin layer or shell on only the outer surface of the support portion advantageously provides a high localized concentration of the active metals on the catalyst outer surface, where it is readily contacted by the amine-containing compounds in the reaction solution. Techniques described in U.S. Pat. No. 5,851,948 (Chuang et al., "Supported Catalyst and Process for Catalytic Oxidation of Volatile Organic Compounds") can be instructive in accordance with these embodiments of the invention.

Catalytic metal can also be deposited on the surface of the support portion according to techniques described by Komiyama et al. ("Concentration Profiles in Impregnation of Porous Catalysts: Nickel on Alumina," J. of Catalysis 63, 35-52 (1980)). Utilizing the principles described by Komiyama et al., radial concentration profiles in the catalyst compositions can be formed by impregnating the support portion with aqueous catalytic metal (e.g., nickel) solutions. In accordance with the present invention, a base can be used with nickel-formate to achieve surface deposition of nickel on alumina supports. More specifically, the pH effect on adsorption has been utilized to achieve surface impregnation of nickel by coimpregnating alumina supports with nickel formate ($Ni(HCOO)_2.2H_2O$) and aqueous ammonia. The result was surface deposition of the nickel on the alumina supports. These principles can be further applied to catalyst compositions including more than one catalytic metal (e.g., more than one of cobalt, nickel, and/or copper).

In still further embodiments, selecting a desirable particle size for the support portion can control internal mass transfer resistance. As discussed in European Patent Application No. EP 1249440 A1 ("Process for Preparing Linear Alkylbenzenes," Wang et al.), both the catalyst particle size and porosity can be adjusted to provide a desired conversion and catalytic stability.

In use, the catalyst composition is added to promote the transamination process. The amount of catalyst composition that is used to promote transamination can be determined based on one or more of the following factors: the type and amount of reactants, the reactor (reaction vessel) configuration, the reaction conditions (such as temperature, time, flow rate, and pressure), the degree of conversion to a desired product(s), and the selectivity desired (i.e., the ratio of the desired product over an undesired product). The catalyst composition is present in the reaction zone in sufficient catalytic amount to enable the desired reaction to occur.

The particulate support may have a so-called guest/host structure, which may be prepared by adsorbing or adhering fine (less than 100 micrometers, preferably less than 50 micrometers and most preferably less than 10 micrometer in size) nanoporous particles on coarser (greater than 30 mesh) particles. The smaller particles are referred to as guests, while the large particles supporting them are referred to as hosts. This small-particle-supported-on-a-larger-particle composite structure provides very high total exterior surface area while retaining the desirable gas passing characteristics, i.e., low pressure drop, of a coarser particle. In addition, by using smaller particles in constructing these composite particles, inexpensive, coarser particles can be used. Thus, very inexpensive, highly active catalyst particles can be prepared since the bulk of the volume of a catalyst bed may be taken up by the inexpensive, underlying, coarser particles.

The catalyst material can be incorporated into or onto the guest and/or host particles. Often, the catalyst material is incorporated mainly onto the guest material before or after the guest/host composite is formed. Guest/host structures and methods of making these are further described in U.S. Publication No. 2005-0095189 A1.

Preferably, the catalyst and/or the supported catalyst composition are calcined prior to use. Generally, calcining can occur in air or an inert atmosphere such as one based upon nitrogen, argon, carbon dioxide, combinations of these, and the like.

Catalyst material may be incorporated into heterogeneous catalyst systems in a variety of ways. In some instances, a catalyst precursor is first provided on the support, and then the precursor can be converted into the catalyst itself afterward. Exemplary procedures are well known in the industry and include solution impregnation, precipitation, vapor deposition such as by PVD or CVD techniques, and the like.

The transamination reaction can be practiced in any suitable reactor. These include batch reactor, continuous fixed bed reactors, slurry bed reactors, fluidized bed reactors, catalytic distillation reactors, combinations of these, and the like. In certain embodiments, a fixed bed reactor is preferred. A fixed bed reactor includes catalyst pellets that are held in place and do not substantially move with respect to fixed reference frame. At least a portion of the reactor feed material passes over (flows past) the catalyst pellets and reacts to form product(s).

The, lower molecular weight cyclic polyamine to be transaminated can be contacted with the catalyst at any suitable temperature(s) that promotes the production of the desired higher molecular weight, cyclic polyamine. Typically, the temperature is maintained below about 350° C., preferably below 300° C. Preferred temperatures are in the range from 100° C. to 220° C., more preferably from 120° C. to 180° C. Below the preferred temperature ranges, the conversion to the desired higher cyclic polyamine may be too slow to be practical for commercial scale production. Above the preferred temperature ranges, selectivity may be reduced to an undue degree, decreasing the yield of the desired cyclic polyamine compound.

Similarly, the transamination reaction can be contacted with catalyst at any suitable pressure(s) that promotes the production of the desired higher molecular weight, cyclic polyamine. Preferably, the pressure is sufficient to maintain the reactor contents in a liquid state as the reaction proceeds. In some instances, the pressure will vary as the reaction proceeds. For instance, ammonia is a by-product of a typical transamination process. The production of ammonia causes the pressure generally to increase as the reaction proceeds in pressure sealed reactors. Ammonia and/or other pressure-increasing products can be removed from the reactor in order to keep the pressure below a desired threshold. Typically, the pressure is at least 100 psi, preferably at least 200 psi, and preferably less than 1000 psi. Within these guidelines, the pressure is typically in the range from 100 psi to 1500 psi, preferably 200 psi to 1200 psi, more preferably 300 psi to 1000 psi. Pressures in the range of 300 psi to 800 psi are most preferred.

In many embodiments, the starting material used will be in liquid form such that no additional solvent is needed. Indeed, in many instances it may be preferred to carry out the desired reaction in the absence of solvent. However, one or more solvents may be used if desired. A variety of solvents or combinations of solvents may be used. Desirably, the solvent is not unduly reactive with the starting material or the resultant higher molecular weight, cyclic polyamine product(s) and does not unduly decompose under the reaction conditions. Some examples of solvents that could be used include saturated hydrocarbons such as pentane, hexane, octane, nonane, decane, or the like; aromatic hydrocarbons such as toluene, benzene, xylene, ether, combinations of these, and the like. Alcohols are desirably avoided, as many of these are capable of reacting with the amine reactants and/or products. If present, the amount of solvent used may vary over a wide range. In a typical instance, the solvent may constitute from about 5 to about 98 weight percent, desirably 10 to 80 weight percent, of the mixture. Optionally when solvent is used, the reaction medium can be diluted to favor intramolecular reactions and, hence, cyclization, relative to intermolecular interactions.

The reactant mixture for the transamination reaction optionally may, and preferably does, include hydrogen. When hydrogen is used, the level of hydrogen can be adjusted to favor the formation of the desired higher cyclic polyamine while minimizing the amount of hydrogenolysis that can lead to alkyl byproducts (e.g., 1-ethylpiperazine). From 0.1 to about 100 mole percent, desirably about 1 to about 10 mole percent of hydrogen per mole of reactants would be suitable.

The one or more cyclic polyamines contained in the reaction product mixture made according to the present invention can be separated (refined) by any method known in the art. For example, the ethyleneamines can be refined using conventional distillation technology known in the art. Preferably, dividing wall columns are used. Other separation techniques such as membrane separation, melt crystallization, and reactive distillation may also be employed. Alternatively, the lower molecular weight polyamine can be removed and recycled back to the reactor, and the higher molecular weight polyamine can be used as a mixture or further separation can be employed to give the products with higher purity.

The present invention will now be further described with reference to the following illustrative examples.

Catalyst Preparation

Unless otherwise noted, the catalyst compositions employed were prepared using the following procedure. Precursor salts of nickel and rhenium were dissolved in 70-80° C. water to form an impregnation solution. The final volume of the impregnation solution was adjusted to equal the adsorption volume required for the number of times that the carrier was impregnated, and the quantities of the precursor salts were calculated to give a nominal composition of 6.8 and 1.8 wt. percent nickel and rhenium, respectively. An alumina/silica (80:20 wt. percent) carrier was impregnated to incipient wetness by the addition of the appropriate amount of impregnation solution and gently agitated until all the liquid was adsorbed. The sample was then calcined in air at 340° C. When the support had cooled, additional impregnations were performed until all of the solution had been added. A calcination step at 340° C. was done after each impregnation. The material was reduced in hydrogen at 340° C. After reduction, the catalyst was passivated with a small amount of oxygen in an inert gas so the material could be handled in air.

Those skilled in the art will readily appreciate that impregnation with the impregnation solution can optionally be performed in one, two, three or more incipient wetness applications, as dictated by such variables as the solubility of the precursor salts, the porosity of the support to be impregnated, and the desired weight loading of the metal.

Reactor/Reaction Conditions

The reaction was run in a 1 inch by 8 foot packed bed reactor with 400 grams of the catalyst described above. The reactor bed was made of 1 inch seamless Swagelok tubing (1 inch outside diameter, 0.095 in wall thickness). The length of the reactor tube was approximately 8 feet. It is incased in 1.5 inch diameter Swagelok tubing through which heat transfer fluid was pumped via a standard laboratory heating bath. This allowed for isothermal operation of the reactor tube. A multipoint thermocouple was inside the reactor bed for temperature monitoring. Temperature and pressure was monitored at various points in the reactor system. The 2-(piperazin-1-yl)ethanamine (AEP) feed material was pumped via a 500 ml Isco syringe pump through a flow meter, a preheater, and into the bottom of the reactor. Just prior to the reactor tube inlet (bottom), the hydrogen gas was introduced to the AEP stream. There was a sampling system that allowed for a timed sample to be taken of the product stream. The sample time was dependent on the feed flowrate, but routinely samples were taken in the range of 5-30 minutes. The sampling system consisted of a stainless reservoir to collect the AEP reaction mixture, followed by a small scrubber, and a wet test meter. This allowed for quantification of the feed flow, ammonia generation, and hydrogen flow during sampling. The product mixture is analyzed by gas chromatography and the peaks identified using electron impact mass spectrometry. In some cases the total weight percent was greater than 100 percent due to different response factors with higher molecular weight oligomers.

EXAMPLES

Reactions were run as described above in the Reactor/Reaction Conditions section. The results of these reactions are set forth in the following tables in which Table 1 shows the difference in the final product mix as a function of AEP space velocity; Table 2 shows the effect on AEP conversion at different reactor pressures and a constant temperature and feed rate; and Table 3 shows that the effect upon BPEA selectivity at various AEP conversions at a constant pressure and feed rate.

TABLE 1

| Product GC Analysis | Condition 1<br>Oil bath at 155 C.<br>AEP feed at 1.5 mL/min.<br>150 sccm of H2 flow.<br>800 psig of pressure | Condition 2<br>Oil bath at 155 C.<br>AEP feed at 3 mL/min.<br>150 sccm of H2 flow.<br>800 psig of pressure |
|---|---|---|
| AEP (wt %) | 30.5 | 53.8 |
| BPEA (wt %) | 61.6 | 42.9 |
| Others (, wt %)* | 14.6 | 9.3 |
| GC Total | 106.7 | 106.0 |
| AEP conversion, % | 68.8 | 44.9 |
| AEP Product (BPEA) Selectivity, % | 80.9 | 82.2 |
| AEP By-Product Selectivity, % | 19.1 | 17.8 |

Others include piperazine, higher cyclic polyamine oligomers, and 2-(4-(2-(piperazin-1-yl)ethyl)piperazin-1-yl)ethanamine.

Table 1 shows that as the feed rate of AEP increases, the AEP conversion to BPEA decreases. However, the selectivity to BPEA remains similar across the AEP conversion range of ca. 30-54 percent.

The invention claimed is:

1. A method of manufacturing a polyfunctional amine selected from bis(2-(piperazin-1-yl)ethyl)amine (BPEA) (3-(piperazin-1-yl)propyl)amine, bis(4-(piperazin-1-yl)butyl)amine, bis(5-(piperazin-1-yl)pentyl)amine, bis(6-(piperazin-1-yl)hexyl)amine, bis(1-(piperazin-1-yl)propan-2-yl)amine, and bis(2-(piperazin-1-yl)propyl)amine, comprising the steps of:

(a) providing an amine selected from 2-(piperazin-1-yl)ethanamine (AEP), 3-(piperazin-1-yl)propan-1-amine, 4-(piperazin-1-yl)butan-1-amine, 5-(piperazin-1-yl)pentan-1-amine, 6-(piperazin-1-yl)hexan-1-amine, 1-(piperazin-1-yl)propan-2-amine and 2-(piperazin-1-yl)propan-1-amine; and (b) reacting the amine in the presence of a hydrogenation/dehydrogenation catalyst under conditions effective to cause the formation of polyfunctional amine, wherein the catalyst is selected from platinum, palladium, rhodium, ruthenium, nickel, iron, copper, chromium, molybdenum, cobalt, osmium, and iridium, and the catalyst optionally comprises a metal promoter selected from Group IA, Group IIA, Group IIIA, Group IVA, Group VA, Group VIA, Group IB, Group JIB Group IIIB, Group IVB, Group VB, Group VIB, Group VIIB and Group VIIIB of the Periodic Table (IUPAC format), and metal oxides thereof.

2. The method of claim 1, wherein the polyfunctional amine is BPEA.

3. The method of claim 1, wherein the amine of subparagraph (a) is AEP.

4. The method of claim 3, wherein reacting is performed to provide an AEP conversion in the range of 20% to 65%.

5. The method of claim 1, wherein the hydrogenation/dehydrogenation catalyst comprises a transamination catalyst selected from nickel (Ni), copper (Cu), cobalt (Co), ruthenium (Ru), rhodium (Rh), palladium (Pd), iridium, and combinations thereof and the metal promoter is selected from copper, cobalt, chromium, rhodium, iridium, ruthenium, zinc, palladium, platinum, sodium, calcium, magnesium, strontium, lithium, potassium, barium, cesium, lanthanum, tungsten, iron, silver, titanium, manganese, niobium, aluminum, tin and mixtures of these metals.

6. The method of claim 5, wherein the transamination catalyst comprises Ni and Re.

7. The method of claim 1, wherein the hydrogenation/dehydrogenation catalyst comprises an alumina/silica carrier.

8. The method of claim 6, wherein the transamination catalyst comprises Ni and Re in a ratio in the range of 3:1 to 14:1 on an alumina-silica support.

9. The method of claim 1, wherein the step of reacting also causes formation of a second higher molecular weight polyfunctional amine selected from 2-(4-(2-(piperazin-1-yl)ethyl)piperazin-1-yl)ethanamine, 3-(4-(3-(piperazin-1-yl)propyl)piperazin-1-yl)propan-1-amine, 4-(4-(4-(piperazin-1-yl)butyl)piperazin-1-yl)butan-1-amine, 5-(4-(5-(piperazin-1-yl)pentyl)piperazin-1-yl)pentan-1-amine, 6-(4-(6-(piperazin-1-yl)hexyl)piperazin-1-yl)hexan-1-amine, 1-(4-(1-(piperazin-1-yl)propan-2-yl)piperazin-1-yl)propan-2-amine, and 2-(4-(2-(piperazin-1-yl)propyl)piperazin-1-yl)propan-1-amine.

10. The method of claim 9, wherein the first polyfunctional amine is BPEA, the second polyfunctional amine is 2-(4-(2-(piperazin-1-yl)ethyl)piperazin-1-yl)ethanamine, and the amine of subparagraph (a) is AEP.

11. The method of claim 1, wherein reacting is performed at a pressure of less than 1000 psi.

12. The method of claim 1, where, in the step reacting, an amount of the amine in the range of 30 to 54% is converted to product.

13. The method of claim 1, wherein the step reacting provides a selectivity to the polyfunctional amine of about 80% or greater.

* * * * *

UNITED STATES PATENT AND TRADEMARK OFFICE
CERTIFICATE OF CORRECTION

PATENT NO.       : 9,162,995 B2
APPLICATION NO.  : 14/369622
DATED            : October 20, 2015
INVENTOR(S)      : Stephen W. King

Page 1 of 1

It is certified that error appears in the above-identified patent and that said Letters Patent is hereby corrected as shown below:

In the claims

<u>Column 15</u>
Line 16, "Group VA, Group VIA, Group IB, Group JIB, Group" should be --Group VA, Group VIA, Group IB, Group IIB, Group--

Signed and Sealed this
Fifth Day of July, 2016

Michelle K. Lee
*Director of the United States Patent and Trademark Office*